US00PP34944P2

(12) United States Plant Patent
Noack

(10) Patent No.: US PP34,944 P2
(45) Date of Patent: Jan. 31, 2023

(54) SHRUB ROSE PLANT NAMED 'NOA39131'

(50) Latin Name: *Rosa hybrida*
Varietal Denomination: 'NOA39131'

(71) Applicant: Reinhard Noack, Gutersloh (DE)

(72) Inventor: Reinhard Noack, Gutersloh (DE)

( * ) Notice: Subject to any disclaimer, the term of this patent is extended or adjusted under 35 U.S.C. 154(b) by 0 days.

(21) Appl. No.: 17/941,749

(22) Filed: Sep. 9, 2022

(51) Int. Cl.
*A01H 5/02* (2018.01)

(52) U.S. Cl.
USPC ..... Plt./105

(58) Field of Classification Search
USPC ..... Plt./105
See application file for complete search history.

*Primary Examiner* — Annette H Para
(74) *Attorney, Agent, or Firm* — Cassandra Bright

(57) ABSTRACT

A new and distinct cultivar of *Rosa* plant for garden use named 'NOA39131' is disclosed, characterized by fully double brilliant golden orange flowers on upright plants with rapid re-flowering. Plants have excellent resistance to blackspot, powdery mildew, downy mildew and rust diseases. Flowers are fragrant and plant rebloom rapidly. The new variety is a *Rosa*, normally produced as an outdoor garden or container plant.

2 Drawing Sheets

Figure 1:
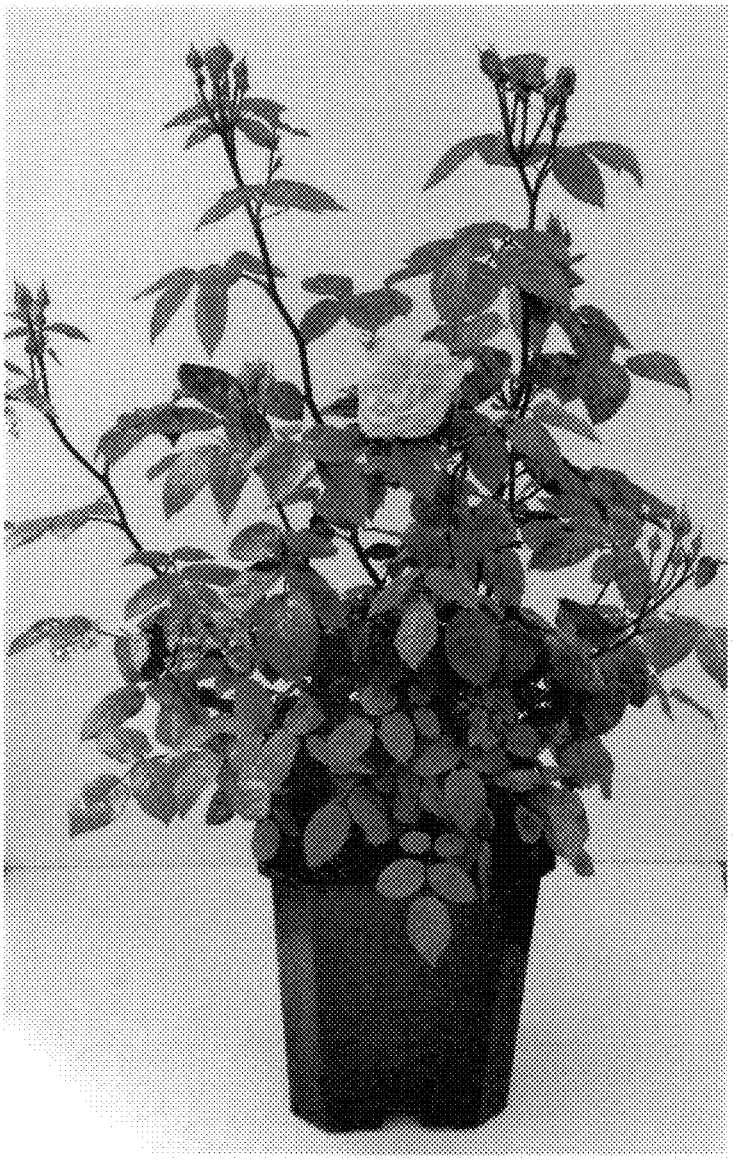

Latin name of the genus and species: *Rosa hybrida.*
Variety denomination: 'NOA39131'.

BACKGROUND OF THE INVENTION

The new *Rosa* cultivar is a product of a planned breeding program conducted by the inventor, Reinhard Noack, conducted in Gutersloh, Germany. The objective of the breeding program was to create new and distinct landscape rose plants with unique qualities such as bright flower colors and excellent resistance to diseases encountered in landscapes and gardens. These objectives have been substantially achieved and in that distinguish 'NOA39131' from all other varieties of which the inventor is aware. This combination of qualities is not present in prior rose cultivars known to the inventor. The cross resulting in this new variety was made during May of 2013.

The seed parent is an unnamed, unpatented, proprietary *Rosa hybrida* variety. The pollen parent is an unpatented, proprietary *Rosa hybrida* named 'Noa75800'. The new variety was selected in April of 2014 by the inventor in a group of seedlings resulting from the 2013 crossing, in a research greenhouse in Gutersloh, Germany.

Asexual reproduction of the new cultivar was performed by terminal semi-soft wood vegetative cuttings. This was first performed at a research greenhouse in Gutersloh, Germany in Summer of 2014 and has shown that the unique features of this cultivar are stable and reproduced true to type in successive generations.

SUMMARY OF THE INVENTION

The cultivar 'NOA39131' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NOA39131' These characteristics in combination distinguish 'NOA39131' as a new and distinct *Rosa* cultivar:

1. Golden orange flowers.
2. Upright plant habit.
3. Plants have excellent resistance to blackspot, powdery mildew, downy mildew and rust foliar diseases.
4. Fragrant flowers.
5. Long lasting individual flowers.
6. Rapid repeat flowering.
7. Easy to grow.

PARENTAL COMPARISON

Plants of the new cultivar 'NOA39131' are similar to plants of the seed parent, in most horticultural characteristics, however, plants of the new cultivar 'NOA39131' differ in the following:

1. The new variety has orange flowers; the seed parent has red flowers.
2. The new variety exhibits better disease resistance than the seed parent.

Plants of the new cultivar 'NOA39131' are similar to plants of the pollen parent in most horticultural characteristics, however, plants of the new cultivar 'NOA39131' differ in the following;

1. Height of the new variety is approximately 90 cm; height of the pollen parent is approximately 60 to 70 cm.
2. Flowers of the new variety are more fragrant than flowers of the pollen parent.
3. Flowers of the new variety are fully double; flowers of the pollen parent are semi-double.

COMMERCIAL COMPARISON

Plants of the new cultivar 'NOA39131' can be compared to the commercial variety *Rosa* 'Korberbeni', unpatented. These varieties are similar in most horticultural characteristics, however 'NOA39131' differs in the following:

1. The new variety has darker, brighter orange flowers than this comparator which has soft orange-yellow flowers.
2. The new variety produces unruffled petals; this comparator has ruffled petals.

Plants of the new cultivar 'NOA39131' can also be compared to the commercial variety *Rosa* 'Fryentice', unpatented. These varieties are similar in most horticultural characteristics; however, 'NOA39131' differs in the following:

1. The new variety produces unruffled petals; this comparator has ruffled petals.
2. Plants of 'NOA39131' are taller than plants of this comparator.

BRIEF DESCRIPTION OF THE PHOTOGRAPHS

The accompanying photograph in FIG. 1 illustrates in full color a typical plant of 'NOA39131'. Age of the plant photographed is approximately 2 years.

Figure 2:
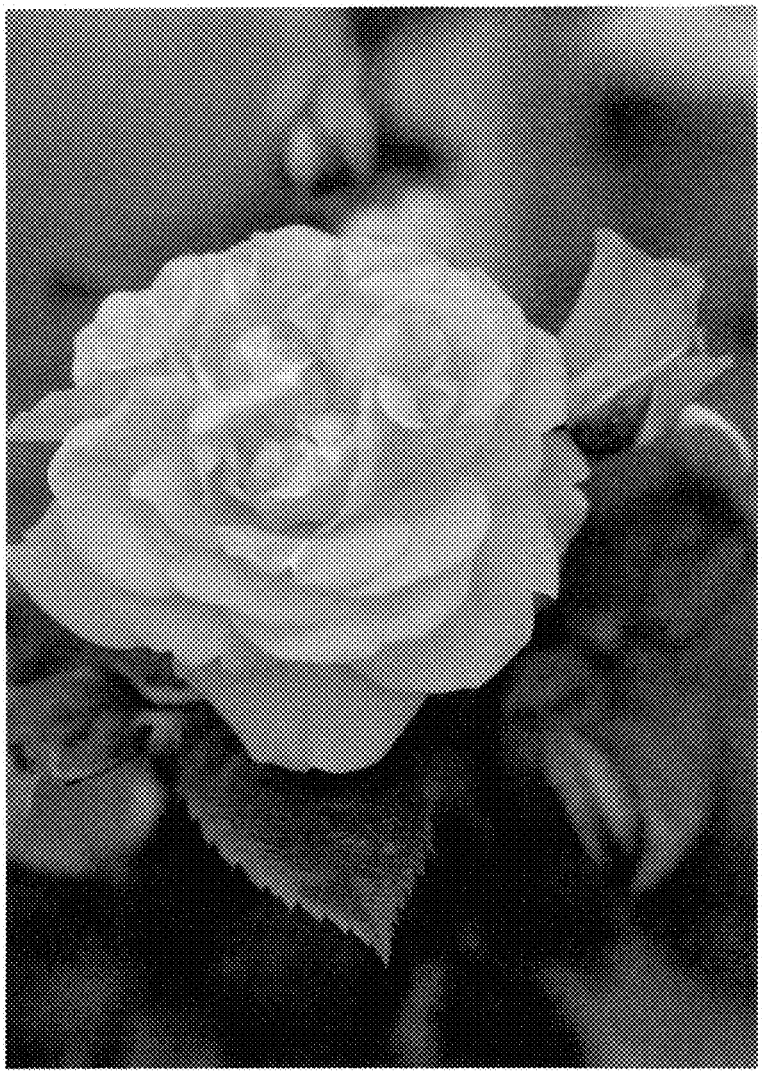

FIG. 2 illustrates a close-up view of the mature flower and flower buds.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1995 except where general terms of ordinary dictionary significance are used. The following observations and measurements describe 'NOA39131' plants grown outdoors, in Gutersloh, Germany. The growing temperature ranged from approximately −1° C. to 35° C. during the day and from approximately −16° C. to 20° C. during the night. General light conditions are bright, normal sunlight. Measurements and numerical values represent averages of typical plant types.

Botanical classification: *Rosa* 'NOA39131'.

*Commercial classification*.—Shrub rose.

PROPAGATION

Time to initiate roots: About 42 days at approximately 20° C.

Time to produce a rooted cutting: About 90 days at approximately 15° C.

PLANT

Age of plant described: Approximately 3 years, planted in the ground.

Growth habit: Upright.

Mature height: 90 cm.

Mature plant spread: 50 cm to 55 cm.

Rootstock: Own root.

Growth rate: Approximately 80 cm to 90 cm per year.

Length of primary lateral branches: Average 75 cm.

Diameter of lateral branches: Approximately 6 mm.

Quantity of lateral branches: Approximately 8-12.

Branching arrangement: Alternate.

Branches-young wood:

*Diameter*.—Approximately 4 to 6 mm.

*Texture*.—Glabrous.

*Color*.—Near Greyed-Red 178B.

Branches-old wood:

*Diameter*.—Approximately 1.5 cm, after 3 years.

*Color*.—Near Green RHS 137C, with brown tinge not accurately described with R.H.S. chart.

*Texture*.—Smooth.

Thorns:

*Density*.—Approximately 10 per 10 cm of stem.

*Color*.—Young: Near Greyed-Orange 171B. Mature: Near Greyed-Orange 165D.

*Shape*.—Deltate.

*Size*.—About 5 to 10 mm in height and 3 to 6 mm at base.

FOLIAGE

Leaf:

*Arrangement*.—Alternate.

*Quantity*.—Approximately 12 per main branch.

*Average length*.—Approximately 14 cm.

*Average width*.—Approximately 9 cm.

Leaflet:

*Quantity*.—Most commonly 5 per leaf. Occasionally 3.

*Average length*.—Approximately 6.8 cm.

*Average width*.—Approximately 3.5 cm.

*Shape of blade*.—Ovate.

*Apex*.—Acuminate.

*Base*.—Obtuse.

*Margin*.—Serrated.

*Appearance of top surface*.—Moderately glossy.

*Appearance of bottom surface*.—Matte.

*Texture of top surface*.—Non-pubescent.

*Texture of bottom surface*.—Non-pubescent.

*Leaf internode length*.—Average 5 cm to 8 cm.

*Color*.—Young foliage upper side: Near Yellow-Green RHS 147A strong anthocyanin flush colored near Greyed-Red 178A and 178B. Anthocyanin strongest along margin. Young foliage under side: Near Yellow-Green RHS 147A covered in very strong anthocyanin flush colored near Greyed-Red 178B and 178C. Mature foliage upper side: Near Green RHS 137C. Mature foliage under side: Near Green RHS 137C. Venation: Type: Pinnate. Venation color upper side: Near Yellow-Green 144C flushed Greyed-Red 178D. Venation color under side: Near Yellow-Green 144C.

Petiole:

*Average length*.—Approximately 3.5 cm.

*Average diameter*.—Approximately 5 mm.

*Color*.—Near RHS Yellow-Green 147C covered in Greyed-Red 178C.

*Texture*.—Glabrous, matte.

Rachis:

*Average length*.—Average range 9.0 to 11.0 cm.

*Average diameter*.—Approximately 5 mm.

*Texture*.—Glabrous.

*Color*.—Near RHS Yellow-Green 147C covered in Greyed-Red 178C.

Stipule:

*Shape*.—Adnate.

*Margin*.—Amplexicaul.

*Apex*.—Tapering.

*Base*.—Truncate.

*Average length*.—Average range 2 to 3 cm.

*Average diameter*.—Approximately 1.0 cm.

*Texture*.—Glabrous.
*Color*.—Near RHS Yellow-Green 147C.

FLOWER

Natural flowering season: Recurrent Spring until mid-Fall.
Begins flowering after how many years/months: As early as 3 months from a rooted liner.
Inflorescence type and habit: Double whorled flowers occurring 3 to 7 per flowering node. Flowers weakly upwardly cupped, having a mostly flat profile. Flowers semi-hemispherical in shape.
Rate of flower opening: Approximately 5 days from bud to fully opened flower.
Lastingness of individual flower: 6 to 8 days after fully opened.
Individual flower size:
*Diameter*.—Approximately 8 cm.
*Depth*.—Approximately 5 cm.
Pedicels:
*Length*.—About 5 to 6 cm.
*Diameter*.—About 3 mm to 4 mm.
*Texture*.—Glabrous, no prickles.
*Color*.—Near RHS Greyed-Red 178B.
Petals:
*Petal arrangement*.—Double whorl, overlapping.
*Size*.—Length: Average 2.5 cm to 3.5. Width: Average 2 cm to 2.5 cm.
*Shape*.—Obovate.
*Margin*.—Entire, non-ruffled.
*Apex*.—Obtuse, rounded, very shallow, broad irregular lobes.
*Base*.—Obtuse.
*Petal quantity*.—Average range 26 to 50.
*Texture*.—Smooth.
Color:
*Petals*.—When opening: Upper surface: Near RHS Orange-Red 32A, Yellow 12B basal spot. Lower surface: Near RHS Orange-Red 32A, Yellow 12B basal spot. Fully opened: Upper surface: Near RHS Orange-Red 32B, 30A near margin, Yellow 12B basal spot. Lower surface: Near RHS Orange-Red 30D, 30A near margin, Yellow 12B basal spot.
Bud:
*Shape*.—Ovate.
*Length*.—Approximately 3 cm.
*Diameter*.—Approximately 1.5 cm.
*Color*.—Near RHS Orange-Red 32A.
Sepals:
*Length*.—2.2 cm.
*Width*.—1.2 cm.
*Shape*.—Lanceolate.
*Apex*.—Apiculate.
*Margin*.—Entire.
*Color*.—Interior Surface: Near RHS Yellow-Green 147B flushed Greyed-Red 179B. Exterior Surface: Near RHS Yellow-Green 147C flushed Greyed-Red 179A.
*Texture*.—Densely puberulent interior and exterior surfaces.
*Sepal extensions*.—Weak.
*Quantity*.—Average 5 per flower.
Receptacle:
*Length*.—1.6 cm.
*Width*.—2.0 to 2.8 cm.
*Shape*.—Pitcher shaped.
*Color*.—Near RHS Green 143C.
Fragrance: Intense.

REPRODUCTIVE ORGANS

Stamens:
*Number*.—Approximately 80.
*Filament length*.—Approximately 3 mm.
*Filament color*.—Near RHS Yellow 13C.
Anthers:
*Length*.—1 mm.
*Shape*.—Narrow ovate.
*Color*.—Near Greyed-Orange 166A.
*Pollen*.—Abundant, colored near Yellow-Orange 15A.
Pistil:
*Number*.—Approximately 10.
*Pistil length*.—Approximately 4 mm.
*Style*.—Length: Approximately 2 mm. Color: Light green to cream, not accurately determined with R.H.S. chart.
*Stigma*.—Shape: Linear. Color: Light green to cream, not accurately determined with R.H.S. chart.

OTHER CHARACTERISTICS

Seeds and fruits: Colored near Green 137C, globular, about 2.5 cm in diameter.
Disease/pest resistance: Excellent resistance to blackspot, powdery mildew, downy mildew and rust. Average resistance to normal pests of garden roses.
Hardiness zone: USDA Zones 5 through 10.

What is claimed is:

1. A new and distinct groundcover rose plant named 'NOA39131' as herein illustrated and described.

* * * * *